US008165377B2

(12) United States Patent
Vaidya et al.

(10) Patent No.: US 8,165,377 B2
(45) Date of Patent: Apr. 24, 2012

(54) SYSTEM AND METHOD FOR DETERMINING A CARDIAC AXIS

(75) Inventors: Vivek Vaidya, Bangalore (IN); Rakesh Mullick, Bangalore (IN); Shekhar Dwivedi, Lucknow (IN); Thomas K. F. Foo, Clifton Park, NY (US); Christopher Judson Hardy, Niskayuna, NY (US); Daniel James Blezek, Rochester, MN (US); Umesha Perdoor Srinivas Adiga, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 741 days.

(21) Appl. No.: 12/323,594

(22) Filed: Nov. 26, 2008

(65) Prior Publication Data

US 2010/0128947 A1 May 27, 2010

(51) Int. Cl.
*G06K 9/00* (2006.01)
*A61B 5/05* (2006.01)

(52) U.S. Cl. ......... 382/131; 382/129; 382/130; 600/425

(58) Field of Classification Search .................. 382/128, 382/129, 130, 131; 600/425
See application file for complete search history.

(56) References Cited

U.S. PATENT DOCUMENTS

| | | | |
|---|---|---|---|
| 4,282,655 A | 8/1981 | Tinman | |
| 5,421,331 A | 6/1995 | Devito et al. | |
| 6,975,897 B2 | 12/2005 | Knoplioch et al. | |
| 7,280,862 B2 | 10/2007 | Gupta et al. | |
| 7,321,676 B2 | 1/2008 | Lavi et al. | |
| 2005/0033143 A1* | 2/2005 | O'Donnell et al. | ............ 600/407 |
| 2005/0113665 A1* | 5/2005 | Mohr et al. | ............ 600/407 |
| 2006/0291705 A1 | 12/2006 | Baumann et al. | |

OTHER PUBLICATIONS

Lelieveldt et al., "Automated Observer-independnent Acquisition of Cardiac Short-Axis MR Images: A Pilot Study," Radiology 2001, 221:537-542.
Lelieveldt et al., "Anatomical Model Matching with Fuzzy Implicit Surfaces for Segmentation of Thoracic Volume Scans," IEEE Trans on Med Imag 1999, 18:218-230.
Jackson et al. "Computerised planning of the acquisition of cardiac MR images," Computerized Medical Imaging and Graphics 28 (2004) 411-418.

* cited by examiner

*Primary Examiner* — Georgia Y Epps
*Assistant Examiner* — Magda Cruz
(74) *Attorney, Agent, or Firm* — Scott J. Asmus (57) ABSTRACT

An apparatus, system and method to determine a coordinate system of a heart includes an imager and a computer. The computer is programmed to acquire a first set of initialization imaging data from an anatomical region of a free-breathing subject. A portion of the first set of initialization imaging data includes organ data, which includes cardiac data. The computer is further programmed to determine a location of a central region of a left ventricle of a heart, where the location is based on the organ data and a priori information. The computer is also programmed to determine a short axis of the left ventricle based on the determined location, acquire a first set of post-initialization imaging data from the free-breathing subject from an imaging plane orientation based on the determination of the short axis, and reconstruct at least one image from the first set of post-initialization imaging data.

12 Claims, 6 Drawing Sheets

SYSTEM AND METHOD FOR DETERMINING A CARDIAC AXIS

BACKGROUND OF THE INVENTION

The present invention relates generally to the determination of the short axis of a heart using an imager and, more particularly, to determining a three-dimensional (3D) coordinate system of a heart using a magnetic resonance (MR) imager.

During MR imaging, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Imaging devices, such as MR devices that implement the principles discussed above, have been used to determine a coordinate system of a heart. That is, imaging devices have been employed to determine the short, vertical long, and the horizontal long axis of the heart. Methods for determining axes of the heart each come with their own drawbacks. For example, a variety of methods for determining the axes of a heart often require an imaging subject to withstand breath-hold techniques so that such determinations are accurate. However, many subjects have difficulties withstanding breath-holds for an appropriate length of time. In addition to breath-hold drawbacks, other drawbacks arise from such methods. For example, a substantial amount of operator instruction is often needed to adequately determine one or more heart axes. In such cases, it is often helpful that such an operator is familiar with cardiac anatomy. As such, the accuracy of axis determinations of a heart is often dependent upon the knowledge of an operator.

It would therefore be desirable to have a system and apparatus that overcomes such aforementioned drawbacks.

BRIEF DESCRIPTION OF THE INVENTION

Embodiments of the invention provide a system and apparatus for determining heart axis information that overcome at least the aforementioned drawbacks.

In accordance with one aspect of the invention, an imaging system to determine a coordinate system of a heart includes an imager and a computer. The computer is programmed to acquire a first set of initialization imaging data from an anatomical region of a free-breathing subject. A portion of the first set of initialization imaging data includes organ data, which includes cardiac data. The computer is further programmed to determine a location of a central region of a left ventricle of a heart, where the first location is based on the organ data and a priori information. The computer is also programmed to determine a short axis of the left ventricle based on the location of the central region of the left ventricle, acquire a first set of post-initialization imaging data from the free-breathing subject from an imaging plane positioned at an orientation based on the determination of the short axis, and reconstruct at least one image from the first set of post-initialization imaging data.

In accordance with another aspect of the invention, a computer readable storage medium having stored thereon a computer program comprising instructions, which when executed by a computer, cause the computer to acquire a first set of initialization imaging data from a free-breathing subject, reconstruct a plurality of images based on the first set of initialization imaging data, determine a location of a portion of an organ in the plurality of images, and determine a three-dimensional (3D) orientation of a left heart ventricle of the free-breathing subject based on statistical information free of subject information and further based on the location of the portion of the organ. The three-dimensional orientation comprises a short axis, a vertical long axis, and a horizontal long axis of the heart. The computer is further caused to acquire a first set of post-initialization imaging data from the free-breathing subject along at least one of the short axis, the vertical long axis, and the horizontal long axis and also reconstruct at least one image based on the acquired first set of post-initialization imaging data.

In accordance with yet another aspect of the invention, a method for determining the orientation of a cardiac region includes acquiring a first set of imaging data from of cardiac region of a free-breathing subject, reconstructing a plurality of images from the first set of imaging data, locating at least a portion of an organ in the plurality of images, and acquiring a second set of imaging data from the free-breathing subject. The imaging data is acquired using a medical imaging device. The method further includes determining a three-dimensional (3D) coordinate system of a left heart ventricle of the free-breathing subject based on the location of the at least a portion of the organ, statistical information free of data acquired from the subject, and the acquired second set of imaging data and also includes determining an imaging plane within the 3D coordinate system of the left ventricle, acquiring a third set of imaging data from the free-breathing subject along the imaging plane, and reconstructing an image from the third set of imaging data.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE PREFERRED EMBODIMENT

Embodiments described herein may be implemented by a variety of imaging apparatuses or systems. For example, embodiments of the invention may be implemented by a magnetic resonance imaging (MRI) apparatus, computed tomography (CT) apparatus, ultrasound apparatus, or the like.

Figure 1:
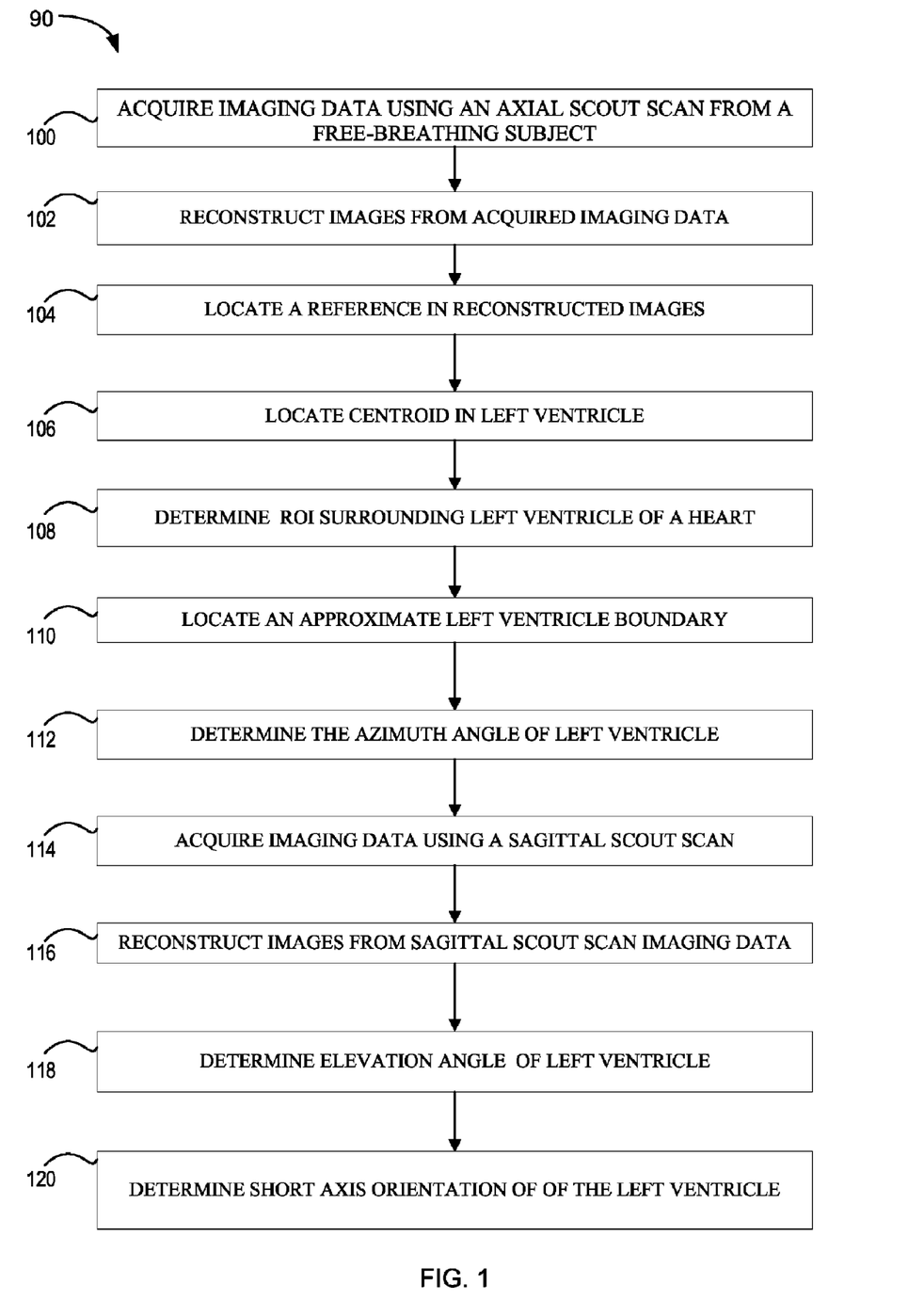
FIG. 1 is a flowchart depicting a technique for automatic determination of a left ventricle short axis according to an embodiment of the invention.

Referring to FIG. 1, a flowchart depicting a technique 90 for the automatic determination of a short axis of a subject heart according to an embodiment of the invention is shown. Starting at BLOCK 100, a first set of initialization imaging data is automatically acquired from a free-breathing subject using an axial scout scan performed by an imaging apparatus. The imaging data (i.e., heart or cardiac data along with any other organ data) is acquired from a region including an anatomical prior or reference and a left ventricle. As such, the first set of initialization data includes left ventricle data and anatomical prior data, which may include heart or cardiac data and/or other organ data. In the present embodiment, a lung portion is used as the anatomical prior or reference. However the use of other anatomical priors to gather other organ data therefrom is contemplated. For example, a heart septum, aorta, myocardium, or the left ventricle itself could be used as an anatomical prior. In one embodiment, it is preferred that the lung portion is the portion of lung located between the heart, spinal cord, and chest fat. After acquiring the first set of imaging data, a plurality of images (i.e., axial images) are automatically reconstructed therefrom at BLOCK 102. Proceeding to BLOCK 104, the reference (i.e., the central region of the left lung portion in the present embodiment) is automatically located in the reconstructed axial images. A variety of techniques may be used to automatically determine the reference location. Following the automatic determination of the central region of the lung portion, process control proceeds to BLOCK 106, where a central portion or centroid of the left ventricle in the axial images is automatically determined from lung portion information obtained at BLOCK 104. In one embodiment, the automatic determination of the location of the centroid of the left ventricle is determined using a heuristic approach along with "a priori" information and the determined location of the central portion of the lung. The a priori information includes information derived from previously determined or acquired statistics of human anatomical shape and size. As such, the a priori information is free of data from the subject, for whom the technique shown in FIG. 1 is being performed. By using the a priori information about the spatial relationship between a lung and a left ventricle along with the information about the location of the central portion of the subject's lung, the location of the left ventricle centroid is automatically determined.

After the location of the left ventricle centroid is located, process control proceeds to BLOCK 108, where a region of interest (ROI) is automatically generated around the left ventricle in the axial images. Once the ROI is generated, the left ventricle boundary within the ROI is automatically determined at BLOCK 110. As such, a left ventricle mask is determined. The manner in which the left ventricle boundary is determined according to an embodiment of the invention will be fully set forth with respect to FIGS. 2-3. After determining the left ventricle boundary, process control proceeds to BLOCK 112, where the azimuth angle (i.e., a degree of rotation) of the left ventricle is automatically determined, in part, from the left ventricle mask. Details regarding the automatic determination of the azimuth angle will be more fully set forth below with respect to FIG. 4.

After determining the azimuth angle of the left ventricle, process control proceeds to BLOCK 114, where a second set of initialization imaging data is automatically acquired from a free-breathing subject using a sagittal scan. The imaging data is acquired from the ROI that was determined or generated at BLOCK 108. Though the flowchart of FIG. 1 depicts the sagittal imaging data acquisition occurring after azimuth angle determination at BLOCK 112, it is contemplated that the sagittal imaging data acquisition may occur prior to azimuth angle determination 112, but after the ROI determination of BLOCK 108.

Still referring to FIG. 1, at BLOCK 116, a plurality of sagittal scan images containing image information about the left ventricle is automatically reconstructed from the second set of initialization imaging data acquired using the sagittal scout scan. As with the sagittal scan image data acquisition 114, it is contemplated that the image reconstruction of such data 116 may occur prior to azimuth angle determination at BLOCK 112, as long as such sagittal image reconstruction is subsequent to the sagittal image data acquisition.

After sagittal image reconstruction 116, the elevation angle of the left ventricle is automatically determined at BLOCK 118. In one embodiment, the elevation angle is determined from a left ventricle mask. An alternate embodiment will be described fully below with respect to FIG. 5. With the left ventricle elevation angle 118, the azimuth angle 112, and the location of the centroid of the left ventricle 104, process control proceeds to BLOCK 120, where the short axis of the left ventricle is automatically determined therefrom.

Accordingly, as described in the embodiment above, the short axis of the left ventricle is automatically determined from data sets acquired from free-breathing subjects. That is, at the push of a button, an axial scout scan free-breathing data set and a sagittal scout scan free-breathing data set are acquired, and the left ventricle short axis is determined or oriented therefrom. Upon the automatic determination of the short axis at BLOCK 120, an operator may initiate post-initialization image data acquisition along a plane oriented along the short axis so that one or more images may be determined therefrom. However, it is also contemplated that such acquisition and reconstruction may be automatic. As such, at a push of a button, an imager may be caused to automatically determine the short axis of the left ventricle and then acquire image data therealong so that one or more images can be reconstructed therefrom. Accordingly, it is not necessary that an operator have an intimate knowledge of the heart and the heart short axis so as to be able to obtain high quality images of the heart along the short axis. As will be discussed with respect to FIG. 6, in addition to having an imager automatically determine a short axis of a left ventricle, an operator may initiate the determination of additional axes of the left ventricle coordinate system.

Figure 2:
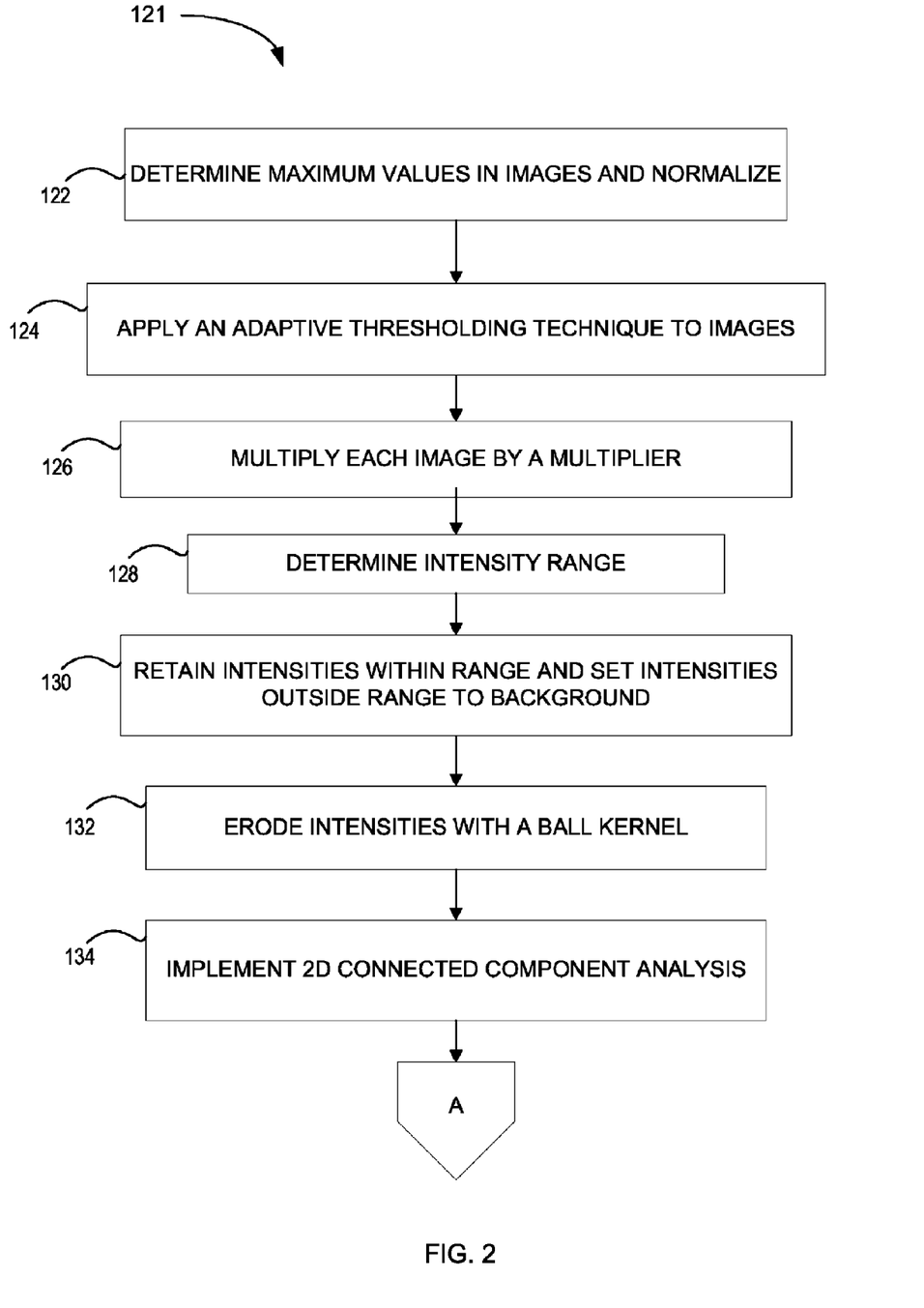
FIGS. 2 and 3 show a flowchart depicting a technique for automatic determination of a left ventricle boundary according to an embodiment of the invention.
Figure 3:
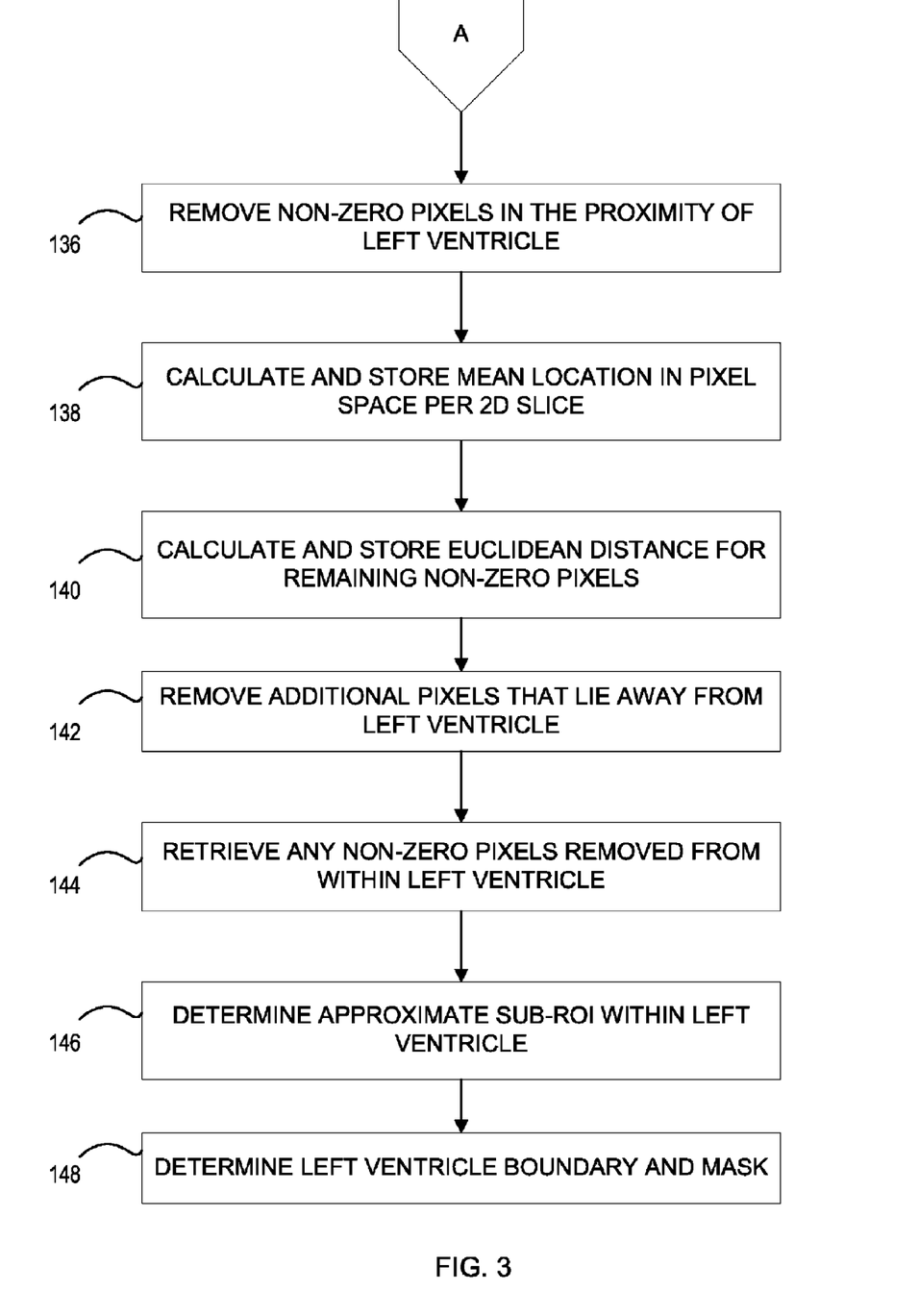

Referring to FIGS. 2 and 3, a flowchart depicting a technique 121 for automatic determination of a left ventricle boundary according to an embodiment of the invention is shown. As discussed above, according to an embodiment of the invention, a left ventricle boundary is automatically determined at BLOCK 110 of FIG. 1. Technique 121 of FIGS. 2 and 3 depict such automatic determination of the left ventricle boundary according to an embodiment of the invention. Starting at BLOCK 122, the automatic determination of the boundary begins with the automatic determination and normalization of the maximum value of each image of the plurality of images reconstructed from the axial scan data (i.e., the plurality of axial images having the ROI of BLOCK 108, FIG. 1 determined therein). After normalizing, process control proceeds to BLOCK 124 of FIG. 2, where an adaptive thresholding operation (i.e., image segmentation) is applied to each image or slice. To increase the dynamic range, images are automatically multiplied by a multiplier such as, for example, one hundred at BLOCK 126. An image intensity range is automatically determined at BLOCK 128. A range of, for example, fifteen to forty-five is preferable. Other ranges, however, are contemplated. Further, it is also contemplated that the range may be predetermined. Once the intensity range is chosen, intensities within the range are retained, and image intensities outside the chosen range become background (i.e., non-left-ventricle data) at BLOCK 130. Process control then proceeds to BLOCK 132, where erosion with a ball kernel of, for example, radius one is automatically implemented on each slice or image. Following erosion, two-dimensional connected component analysis is automatically implemented on each slice at BLOCK 134.

Process control proceeds to BLOCK 136 of FIG. 3, where a selection and rearrangement of non-zero pixels is automatically implemented such that many non-zero pixels in the general proximity of the left ventricle are removed. In one embodiment, the selection and rearrangement of non-zero pixels is achieved through the use of a heuristics approach that sets forth that "left ventricle is towards left and right ventricle is towards right." The use of other similar heuristic statements is also contemplated. Proceeding to BLOCK 138, a mean location of each non-zero pixel in pixel space per two-dimensional slice is then automatically calculated and stored. Next, the Euclidean distance of each remaining non-zero pixel from the mean is calculated and sorted at BLOCK 140. Using the sorted and calculated information, additional pixels that lie away from the left ventricle are automatically removed at BLOCK 142. Process control then proceeds to BLOCK 144, where any non-zero pixels removed from within the left ventricle region are automatically retrieved by equation fitting on the remaining sub area. The sub area generally lies within the left ventricle region. At BLOCK 146, a sub-ROI is determined by automatically fitting a bounding box the sub area. Process control then proceeds to BLOCK 148, where the left ventricle boundary and mask is automatically determined. To determine the left ventricle boundary, the maximum and minimum locations in the bounding box (i.e., the sub ROI) are linearly shifted per each two-dimensional slice. The maximum and minimum locations represent a major and minor axis of an approximate ellipse. The major and minor axis of the ellipse are then automatically plotted to fit the left ventricle region, thus determining an approximate left ventricle boundary. Since the left ventricle boundary is known, a left ventricle mask may be determined therefrom. As such, the left ventricle boundary and mask are automatically determined or located in the axial images at BLOCK 148 based on the location of the centroid of the left ventricle.

Figure 4:
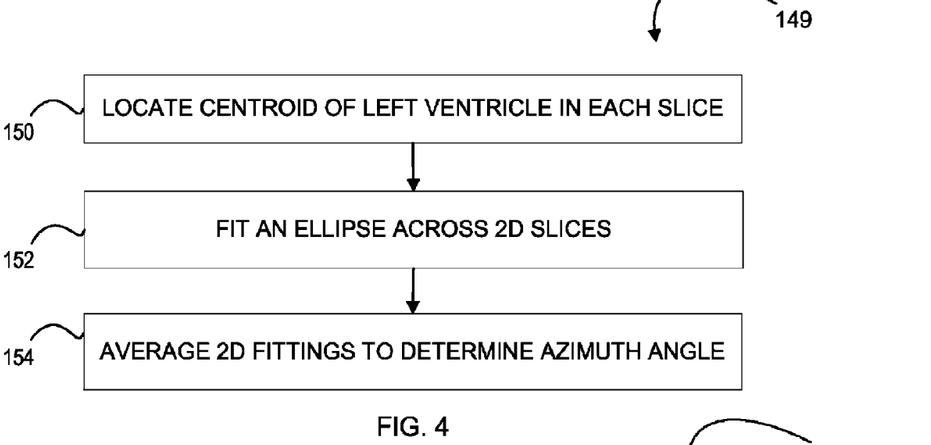
FIG. 4 is a flowchart depicting a technique for automatic determination of a left ventricle azimuth angle according to an embodiment of the invention.

Referring now to FIG. 4, a flowchart depicting a technique 149 for automatic determination of a left ventricle azimuth angle according to an embodiment of the invention is shown. As discussed above, according to an embodiment of the invention, a left ventricle azimuth angle is automatically determined at BLOCK of 112 of FIG. 1. Technique 149 of FIG. 4 depicts such automatic determination of the left ventricle azimuth angle according to an embodiment of the invention. In one embodiment, a principal component analysis technique is implemented. In such embodiment, technique 149 begins with BLOCK 150, where the centroid of the left ventricle found in each slice is automatically located based on the z-direction location of the centroid of the left ventricle. After the location of the centroid of the left ventricle is located in a plurality of the axial images, an ellipse is automatically fitted to an approximate left ventricle mask across a plurality of the 2D slices at BLOCK 152. Process control then proceeds to BLOCK 154, where the average of the 2D fittings is automatically computed to determine the azimuth.

Figure 5:
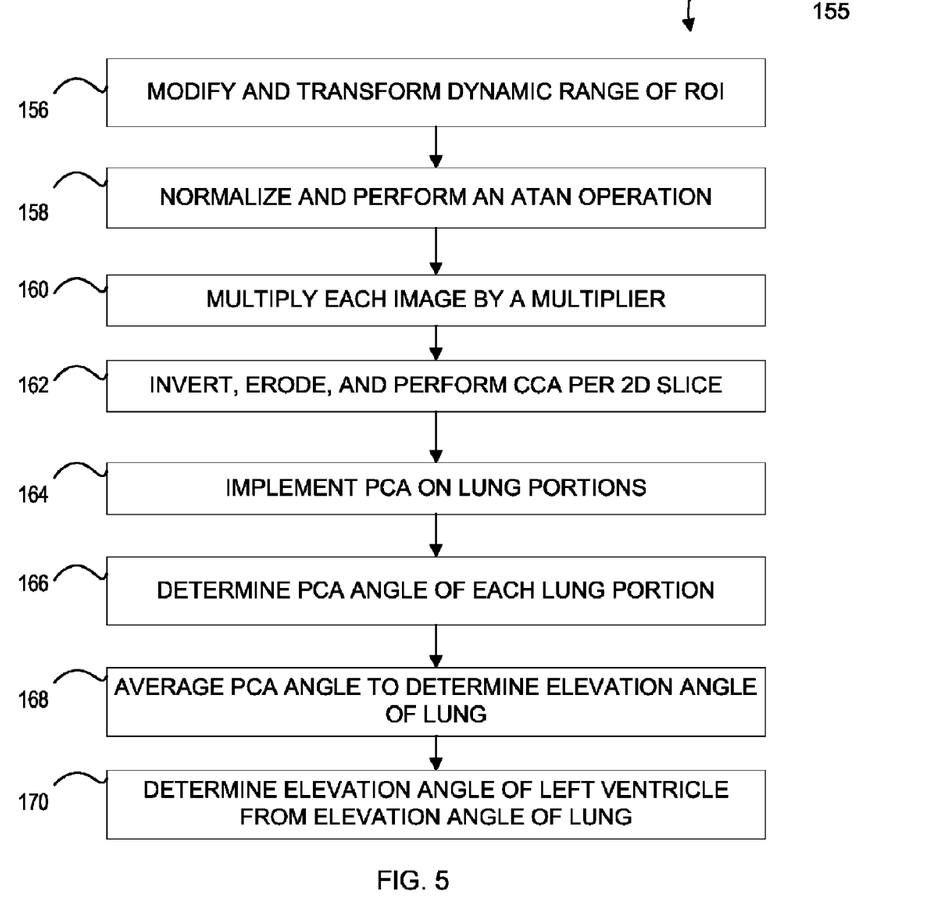
FIG. 5 is a flowchart depicting a technique for automatic determination of a left ventricle elevation angle according to an embodiment of the invention.

Referring to FIG. 5, a flowchart depicting a technique 155 for automatic determination of a left ventricle elevation angle according to an embodiment of the invention is shown. As set forth in BLOCK 118 of FIG. 1, a left ventricle elevation angle is automatically determined before a short axis of the left ventricle is automatically determined. As also discussed above with respect to FIG. 1, the elevation angle of the left ventricle may be automatically determined from a left ventricle mask. However, if such a determination is deemed to be corrupt, an elevation angle of the lung may be used to determine the elevation angle of the left ventricle. That is, the automatic determination of the elevation angle of the left ventricle may instead be based on the elevation angle of the lung. Technique 155 of FIG. 5 depicts such an automatic determination of the left ventricle elevation angle based on a left lung elevation angle, according to an embodiment of the invention. Technique 155 begins at BLOCK 156, where the dynamic range of the ROI in the sagittal images is automatically modified and transformed. In one embodiment, the dynamic range is modified to zero to seventy-eight. Other modified ranges, however, are contemplated. Such regions are then normalized and an arctangent or at an operation is performed thereon at block 158. Process control then proceeds to BLOCK 160, where the sagittal images are multiplied by a multiplier. In one embodiment, the multiplier is ten. However, it is contemplated that other multipliers may also be used. Next, the images or 2D slices are inverted, eroded, and a connected component analysis (CCA) is performed thereon at BLOCK 162. A partial component analysis (PCA) is then automatically implemented on the lung portions in the sagittal images at BLOCK 164. The angle of the partial component analysis for each sagittal image is then automatically determined or calculated from the x-axis at BLOCK 166. Upon determining or calculating these angles, the average elevation angle of the lung in each sagittal image is automatically determined at BLOCK 168. Process control then proceeds to BLOCK 170, where the elevation angle of the left ventricle is then automatically determined from a linear relation that is generated statistically from a priori information such that the elevation angle of the left ventricle is derived from the elevation angle of the lung portion and an ellipse fit to the left ventricle in the plurality of sagittal images. As such, using the determined left ventricle elevation angle, the determined azimuth angle, and the centroid of the left ventricle, the short axis can be determined therefrom.

As discussed above with respect to FIG. 1, in addition to having the imaging apparatus or device automatically determine the short axis of the left ventricle, an operator may choose to initiate the determination of additional axes of the left ventricle coordinate system. That is, an operator may choose to have an imaging apparatus automatically determine the short axis and the vertical long axis of a left ventricle coordinate system; thus, creating a two-dimensional coordinate system of a heart or left ventricle thereof. Further, an operator may choose to cause an imaging apparatus to automatically determine the short, vertical long, and horizontal long axes of a left ventricle coordinate system; thus, creating a three-dimensional coordinate system of a heart or left ventricle thereof.

Figure 6:
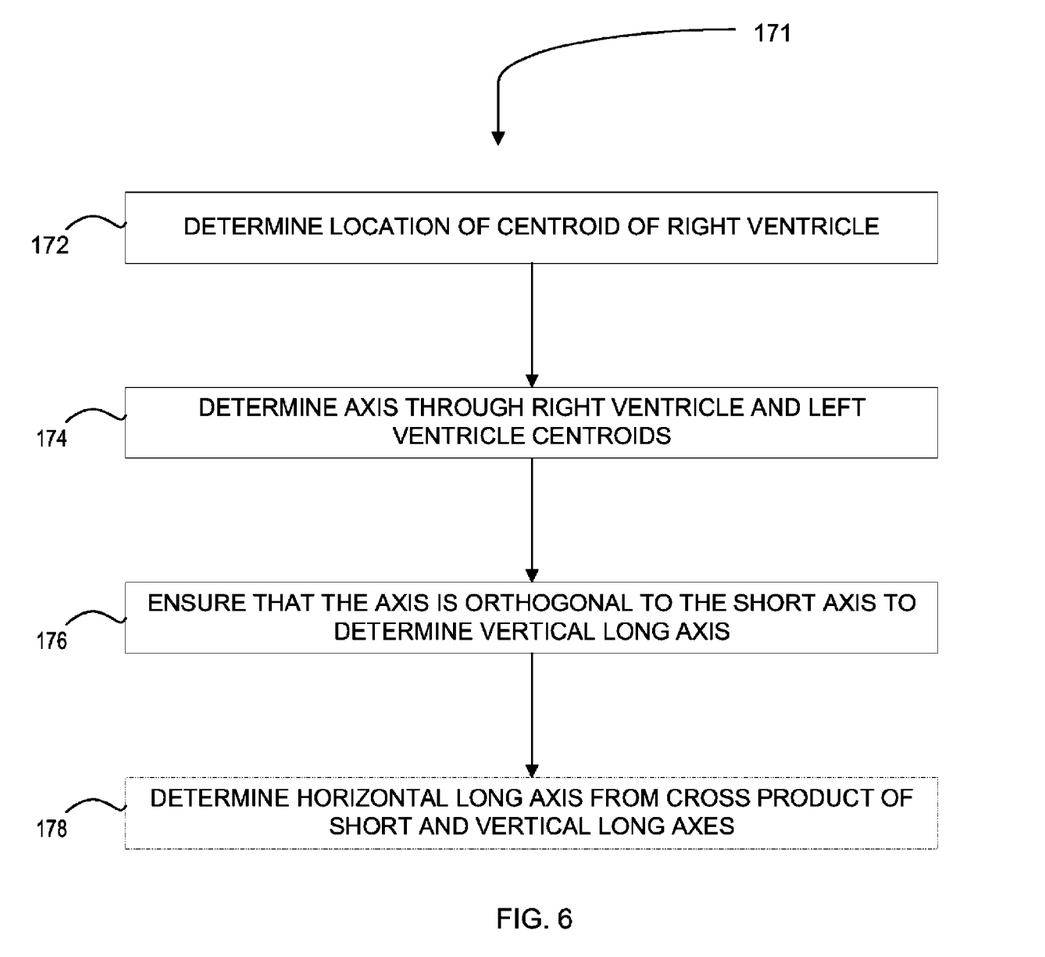
FIG. 6 is a flowchart depicting a technique for automatic determination of multiple axes of a left ventricle according to embodiments of the invention.

As such, referring to FIG. 6, a flowchart depicting a technique 171 for automatic determination of multiple axes of a left ventricle according to according to an embodiment of the invention is shown. Technique 171 begins at BLOCK 172, where process control begins with the automatic determination of the location of the centroid of a right ventricle. Similar to the determination of the centroid of the left ventricle, the determination of the centroid of the right ventricle is based on the location of a central portion of the right lung and a priori information. That is, from the reconstructed axial images of BLOCK 102 of FIG. 1, the central portion of a right lung (i.e., a reference) is located. Using the location of the central portion of the right lung and the a priori statistical information related to human anatomy, the centroid of the right ventricle is determined therefrom at BLOCK 172. Having the location of the centroid of the left ventricle from BLOCK 106 of FIG. 1, and now the location of the centroid of the right ventricle from BLOCK 172 of FIG. 6, process control proceeds to 174, where an axis between the left and right ventricle centroids is automatically determined. Such an axis is an approximate vertical long axis of the left ventricle. At BLOCK 176, the approximate vertical long axis is automatically orthoginalized with the previously determined short axis from BLOCK 120 of FIG. 1 such that an accurate determination of the vertical long axis is determined therefrom. Accordingly, a two-dimensional coordinate system is automatically determined from two free-breathing data sets. As such, two chamber views of a subject heart can be generated using the automatically determined vertical long axis of the corresponding two-dimensional coordinate system.

As discussed above, embodiments of the invention can be used to determine a one- or two-dimensional coordinate system, of the heart or left ventricle. However, as also discussed above with respect to FIG. 1, embodiments of the invention can also be used to determine a three-dimensional coordinate system of the left ventricle. For example, as shown in phantom at BLOCK 178, it is contemplated that a horizontal long axis of the left ventricle may also be automatically determined or oriented. In one embodiment, the cross-product of the short axis and the determined vertical long axis is taken to determine the horizontal long axis. As such, a complete three-dimensional coordinate system of the left ventricle may be automatically determined at the push of a button. A variety of heart views can be generated using the horizontal long axis and/or the three dimensional coordinate system of the left ventricle. For example, by using the horizontal long axis, four chamber views of the heart can be generated therealong.

Upon determination of the two-dimensional or three-dimensional coordinate system, an operator may cause an imager to acquire image data along one or more planes oriented along one of more of the determined axes such that images may be reconstructed therefrom. However, it is also contemplated that the acquisition of image data along planes of the one or more axes could be automatic, followed by automatic reconstruction of images therefrom. Accordingly, an operator may, at the push of a button, cause an imager to automatically determine one or more heart axes and automatically acquire imaging data along the one or more axes such that one or more images can be automatically reconstructed therefrom. As such, a patient merely needs to be positioned relative to the scanner so that images along the one or more heart axis can be automatically obtained therefrom. As with the embodiment described above with respect to FIG. 1, the embodiments described in FIG. 6 do not need an operator having an intimate knowledge of the heart axes to cause an imager to determine such axes and obtain images therealong.

Figure 7:
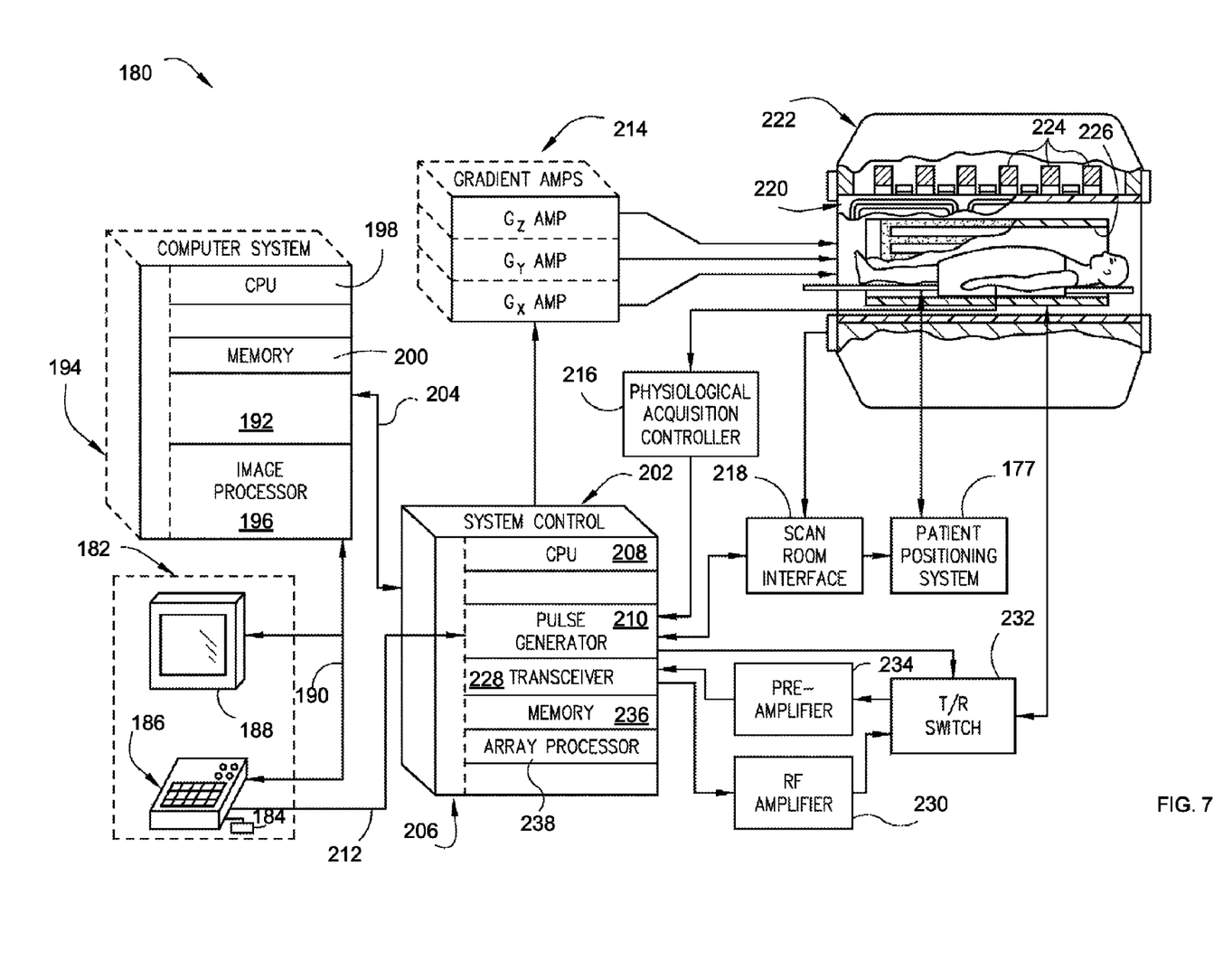
FIG. 7 is a diagram of an exemplary imager that may be used according to an embodiment of the invention.

As discussed above, embodiments of the invention may be implemented using a variety of imaging devices or system. As exemplary imaging device is depicted in FIG. 7, in which the major components of a magnetic resonance imaging (MRI) system 180 that can implement embodiments of the invention is shown. The operation of the system is controlled from an operator console 182 which includes a 184, a control panel 186, and a display screen 188. The console 182 communicates through a link 190 with a separate computer system 192 that enables an operator to control the production and display of images on the display screen 188. The computer system 192 includes a number of modules which communicate with each other through a backplane 194. These include an image processor module 196, a CPU module 198 and a memory module 200, known in the art as a frame buffer for storing image data arrays. The computer system 192 communicates with a separate system control 202 through a high speed serial link 204. The input device 184 can include a mouse, joystick, keyboard, track ball, touch activated screen, light wand, voice control, or any similar or equivalent input device, and may be used for interactive geometry prescription.

The system control 202 includes a set of modules connected together by a backplane 206. These include a CPU module 208 and a pulse generator module 210 which connects to the operator console 182 through a serial link 212. It is through link 212 that the system control 202 receives commands from the operator to indicate the scan sequence that is to be performed. The pulse generator module 210 operates the system components to carry out the desired scan sequence and produces data which indicates the timing, strength and shape of the RF pulses produced, and the timing and length of the data acquisition window. The pulse generator module 210 connects to a set of gradient amplifiers 214, to indicate the timing and shape of the gradient pulses that are produced during the scan. The pulse generator module 210 can also receive patient data from a physiological acquisition controller 216 that receives signals from a number of different sensors connected to the patient, such as ECG signals from electrodes attached to the patient. And finally, the pulse generator module 210 connects to a scan room interface circuit 218 which receives signals from various sensors associated with the condition of the patient and the magnet system. It is also through the scan room interface circuit 218 that a patient positioning system 177 receives commands to move the patient to the desired position for the scan.

The gradient waveforms produced by the pulse generator module 210 are applied to the gradient amplifier system 214 having Gx, Gy, and Gz amplifiers. Each gradient amplifier excites a corresponding physical gradient coil in a gradient coil assembly generally designated 220 to produce the magnetic field gradients used for spatially encoding acquired signals. The gradient coil assembly 220 forms part of a magnet assembly 222 which includes a polarizing magnet 224 and a whole-body RF coil 226. A transceiver module 228 in the system control 202 produces pulses which are amplified by an RF amplifier 230 and coupled to the RF coil 226 by a transmit/receive switch 232. The resulting signals emitted by the excited nuclei in the patient may be sensed by the same RF coil 226 and coupled through the transmit/receive switch 232 to a preamplifier 234. The amplified MR signals are demodulated, filtered, and digitized in the receiver section of the transceiver 228 transmit/receive switch 232 is controlled by a signal from the pulse generator module 210 to electrically connect the RF amplifier 230 to the coil 226 during the transmit mode and to connect the preamplifier 234 to the coil 226 during the receive mode. The transmit/receive switch 232 can also enable a separate RF coil (for example, a surface coil) to be used in either the transmit or receive mode.

The MR signals picked up by the RF coil 226 are digitized by the transceiver module 228 and transferred to a memory module 236 in the system control 202. A scan is complete when an array of raw k-space data has been acquired in the memory module 236. This raw k-space data is rearranged into separate k-space data arrays for each image to be reconstructed, and each of these is input to an array processor 238 which operates to Fourier transform the data into an array of image data. This image data is conveyed through the serial link serial link 204 to the computer system 192 where it is stored in memory. In response to commands received from the operator console 182, this image data may be archived in long term storage or it may be further processed by the image processor 196 and conveyed to the operator console 182 and presented on the display 188.

A technical effect of for the disclosed method and apparatus is that it provides for a processor implemented cardiac axis determination and imaging therealong.

In accordance with one embodiment, an imaging system to determine a coordinate system of a heart includes an imager and a computer. The computer is programmed to acquire a first set of initialization imaging data from an anatomical region of a free-breathing subject. A portion of the first set of initialization imaging data includes organ data, which includes cardiac data. The computer is further programmed to determine a location of a central region of a left ventricle of a heart, where the first location is based on the organ data and a priori information. The computer is also programmed to determine a short axis of the left ventricle based on the location of the central region of the left ventricle, acquire a first set of post-initialization imaging data from the free-breathing subject from an imaging plane positioned at an orientation based on the determination of the short axis, and reconstruct at least one image from the first set of post-initialization imaging data.

In accordance with another embodiment, a computer readable storage medium having stored thereon a computer program comprising instructions, which when executed by a computer, cause the computer to acquire a first set of initialization imaging data from a free-breathing subject, reconstruct a plurality of images based on the first set of initialization imaging data, determine a location of a portion of an organ in the plurality of images, and determine a three-dimensional (3D) orientation of a left heart ventricle of the free-breathing subject based on statistical information free of subject information and further based on the location of the portion of the organ. The three-dimensional orientation comprises a short axis, a vertical long axis, and a horizontal long axis of the heart. The computer is further caused to acquire a first set of post-initialization imaging data from the free-breathing subject along at least one of the short axis, the vertical long axis, and the horizontal long axis and also reconstruct at least one image based on the acquired first set of post-initialization imaging data.

In accordance with yet another embodiment, a method for determining the orientation of a cardiac region includes acquiring a first set of imaging data from of cardiac region of a free-breathing subject, reconstructing a plurality of images from the first set of imaging data, locating at least a portion of an organ in the plurality of images, and acquiring a second set of imaging data from the free-breathing subject. The imaging data is acquired using a medical imaging device. The method further includes determining a three-dimensional (3D) coordinate system of a left heart ventricle of the free-breathing subject based on the location of the at least a portion of the organ, statistical information free of data acquired from the subject, and the acquired second set of imaging data and also includes determining an imaging plane within the 3D coordinate system of the left ventricle, acquiring a third set of imaging data from the free-breathing subject along the imaging plane, and reconstructing an image from the third set of imaging data.

The present invention has been described in terms of the preferred embodiments, and it is recognized that equivalents, alternatives, and modifications, aside from those expressly stated, are possible and within the scope of the appending claims.

What is claimed is:

1. An imaging system to determine a coordinate system of a heart comprising:
an imager; and
a computer programmed to:
acquire a first set of initialization imaging data from an anatomical region of a free-breathing subject, wherein a portion of the first set of imaging data comprises organ data comprising cardiac data;
determine a location of a central region of a left ventricle of a heart based on the organ data and a priori information;
determine a location of a central region of a right ventricle of the heart based on the organ data and the a priori information;
determine a vertical long axis of the heart based on the locations of the central regions of the left and right ventricles;
determine a short axis of the left ventricle based on the location of the central region of the left ventricle;
acquire a first set of post-initialization imaging data from the free-breathing subject from an imaging plane positioned at an orientation based on the determination of the short axis; and
reconstruct at least one image from the first set of post-initialization imaging data.

2. The imaging system of claim 1 wherein the organ data further comprises lung data.

3. The imaging system of claim 1 wherein the imager is one of a magnetic resonance imager, a computed tomography imager, and an ultrasound imager.

4. The imaging system of claim 1 wherein the computer is programmed to acquire the first set of imaging data using an axial scan.

5. The imaging system of claim 1 wherein the imaging plane orientation is further based on the determination of the vertical long axis, and wherein the at least one image is a two chamber view of the heart.

6. The imaging system of claim 1 wherein the computer is further programmed to determine a horizontal long axis of the heart based on the short axis and the vertical long axis, wherein the short axis, the vertical long axis, and the horizontal long axis together comprise a full coordinate system of the heart.

7. The imaging system of claim 6 wherein the imaging plane orientation is further based on the determination of the horizontal long axis, and wherein the at least one image is a four chamber view of the heart.

8. The imaging system of claim 1 wherein the cardiac data comprises at least one of septum data, aorta data, and myocardium data.

9. The imaging system of claim 1 wherein the computer is further programmed to determine an elevation angle and an azimuth angle of the left ventricle, and wherein the computer is programmed to determine the short axis of the left ventricle further based on the elevation angle and the azimuth angle of the left ventricle.

10. The imaging system of claim 9 wherein the first set of initialization imaging data is acquired using an axial scan, and wherein the computer is further programmed to:
  reconstruct a plurality of axial scan images from the acquired first set of initialization imaging data;
  determine the location of the central region of the left ventricle in the plurality of images; and
  fit an ellipse to the left ventricle in the plurality of axial scan images, wherein the determination of the azimuth angle is based on the ellipse fit to the plurality of axial scan images.

11. The imaging system of claim 10 wherein the computer is further programmed to:
  acquire a second set of initialization imaging data from the free-breathing subject using a sagittal scan;
  reconstruct a plurality of sagittal scan images from the second set of initialization imaging data;
  fit an ellipse to the left ventricle in the plurality of sagittal scan images; and
  wherein the determination of the elevation angle is based on the ellipse fit to the plurality of sagittal scan images.

12. The imaging system of claim 1 wherein the computer is further programmed to:
  receive a single user input; and
  automatically acquire the first set of imaging data, automatically determine the location of the central region, and automatically determine the short axis of the left ventricle from the single user input.

* * * * *